United States Patent
Hillairet et al.

(10) Patent No.: US 8,497,331 B2
(45) Date of Patent: Jul. 30, 2013

(54) POLYMERISATION OF ETHYLENE AND ALPHA-OLEFINS WITH PYRROL-IMINOPHENOL COMPLEXES

(75) Inventors: Caroline Hillairet, Soignies (BE); Guillaume Michaud, Lille (FR); Sabine Sirol, Horrues (BE)

(73) Assignee: Total Petrochemicals Research Feluy, Seneffe (Feluy) (BE)

( * ) Notice: Subject to any disclaimer, the term of this patent is extended or adjusted under 35 U.S.C. 154(b) by 202 days.

(21) Appl. No.: 12/516,204

(22) PCT Filed: Nov. 9, 2007

(86) PCT No.: PCT/EP2007/062112
§ 371 (c)(1),
(2), (4) Date: Sep. 29, 2009

(87) PCT Pub. No.: WO2008/061901
PCT Pub. Date: May 29, 2008

(65) Prior Publication Data
US 2010/0063229 A1    Mar. 11, 2010

(30) Foreign Application Priority Data

Nov. 24, 2006 (EP) ..................... 06124707

(51) Int. Cl.
*C08F 4/52* (2006.01)
*C08F 4/64* (2006.01)
*C08F 4/76* (2006.01)
*C08F 4/78* (2006.01)
*B01J 31/00* (2006.01)

(52) U.S. Cl.
USPC ........... 526/161; 526/172; 526/160; 526/170; 526/131; 526/134; 526/133; 526/348; 526/352; 502/103; 502/104

(58) Field of Classification Search
USPC .............................. 556/51; 526/170, 161, 172
See application file for complete search history.

(56) References Cited

U.S. PATENT DOCUMENTS 6,927,261 B2 *   8/2005  Shih .............................. 526/89

FOREIGN PATENT DOCUMENTS

| DE | 99 556 | * | 8/1973 |
| DE | 99556 | | 8/1973 |
| EP | 1426385 | | 6/2004 |
| WO | WO9842665 | | 10/1998 |
| WO | WO2004/081020 | | 9/2004 |
| WO | WO 2004/081020 A1 | * | 9/2004 |

OTHER PUBLICATIONS

Mix et al. DD 99 556 (Aug. 12, 1973); OCR translation in English.*

* cited by examiner

*Primary Examiner* — Rip A. Lee

(57) ABSTRACT

The present invention relates to the field of single site catalyst systems based on pyrrol-iminophenol, pyrrol-iminoalcohol or pyrrol-iminoamine complexes and suitable for oligomerising or homo- or co-polymerising ethylene and alpha-olefins.

36 Claims, No Drawings

POLYMERISATION OF ETHYLENE AND ALPHA-OLEFINS WITH PYRROL-IMINOPHENOL COMPLEXES

CROSS-REFERENCE TO RELATED APPLICATIONS

This application claims the benefit of PCT/EP2007/062112, filed Nov. 9, 2007, which claims priority from EP 06124707.8, filed Nov. 24, 2006.

The present invention relates to the field of single site catalyst systems based on pyrrole-iminophenol, pyrrole-iminoalcohol or pyrrole-iminoamine complexes and suitable for oligomerising or polymerising ethylene and alpha-olefins.

A multitude of catalyst systems available for polymerising or oligomerising ethylene and alpha-olefins exist, but there is a growing need for finding new systems capable of tailoring polymers with very specific properties. More and more post-metallocene catalyst components based on early or late transition metals from Groups 3 to 10 of the Periodic Table have recently been investigated such as for example those disclosed in Gibson and al. review (Gibson, V. C.; Spitzmesser, S. K., in Chem. Rev. 2003, 103, p. 283).

Pyrrol-iminophenol derivatives are known and have been described for example by Schilde (Sawusch, N. Jager, U. Schilde and E. Uhlemann in *Structural Chemistry*, Vol. 10, No. 2, 1999 p. 105), Bhattacharya (Basu, Semanti; Pal, Indrani; Butcher, Ray J.; Rosair, Georgina; Bhattacharya, Samaresh in *Journal of Chemical Sciences*, 2005, 117(2), p. 167) but corresponding complexes have never been described as catalysts for the polymerisation of olefins.

There is still a need to improve either the specificities or the performances of these systems.

It is an aim of this invention to provide new single site catalysts based on tridentate pyrrol-iminophenol, pyrrol-iminoalcohol or pyrrol-iminoamine.

It is another aim of the present invention to provide active catalyst systems based on these catalyst components.

It is a further aim of the present invention to provide a process for polymerising or for oligomerising ethylene and alpha-olefins with these new catalyst systems.

Any one or more of these aims is fulfilled, at least partially, by the present invention.

Accordingly, the present invention discloses metallic complexes of formula I

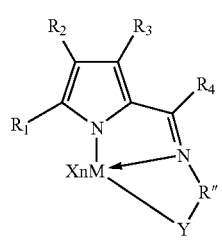

wherein $R_1$, $R_2$, $R_3$, $R_4$, $R_5$, $R_6$, $R_7$, $R_8$, $R_9$, $R_{10}$, $R_{11}$ and $R_{12}$ are each independently selected from hydrogen, unsubstituted or substituted hydrocarbyl having from 1 to 20 carbon atoms, or inert functional group. Two or more of those groups can themselves be linked together to form further ring or rings;
wherein M is a metal Group 3 to 10 of the Periodic Table;
wherein Y is O or NR*, with R* being alkyl or aryl group having from 1 to 12 carbon atoms;
wherein each X can be the same or different and is selected from halogen, substituted or unsubstituted hydrocarbyl having from 1 to 20 carbon atoms, substituted or unsubstituted aryloxy or alkoxy;
wherein m is zero or an integer from 1 to 3;
wherein (n+2) is the valence of M; and
wherein

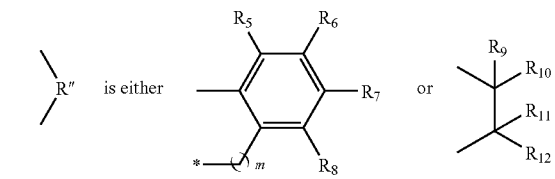

The metallic complex results from the complexation of a ligand of general formula II with metallic salt $MX_{n+2}$ in a solvent

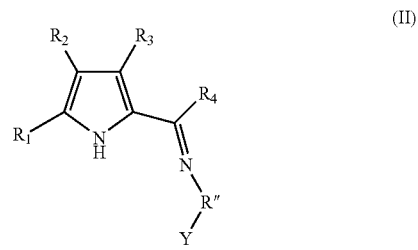

wherein $R_1$ to $R_{12}$, M, X, R" and m are as described hereabove.

Ligand of formula II is the reaction product of carbonylated pyrrole of formula III with compound of formula IV or IV',

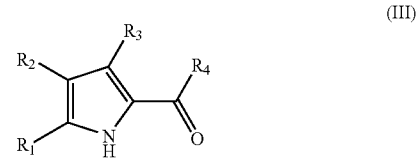

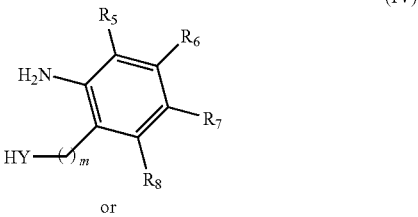

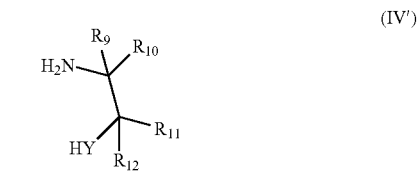

wherein $R_1$ to $R_{12}$ and m are as described hereabove.

The reaction conditions are well known in the art.

By inert functional group, is meant a group, other than hydrocarbyl or substituted hydrocarbyl, that is inert under the complexation conditions to which the compound containing said group is subjected. They can be selected for example from halo, ester, ether, amino, imino, nitro, cyano, carboxyl, phosphate, phosphonite, phosphine, phosphinite, thioether and amide. Preferably, they are selected from halo, such as chloro, bromo, fluoro and iodo, or ether of formula —OR* wherein R* is unsubstituted or substituted hydrocarbyl. After metallation of the ligand, an inert functional group must not coordinate to the metal more strongly than the groups organised to coordinate to the metal and thereby displace the desired coordinating group.

In preferred embodiments according to the present invention, m is zero and $R_2$, $R_3$, $R_4$, $R_8$, $R_9$ and $R_{11}$ are hydrogen and $R_1$, $R_5$, $R_6$, $R_7$, $R_{10}$ and $R_{12}$ can each be independently selected from hydrogen, substituted or unsubstituted hydrocarbyl having from 1 to 20 carbon atoms, halogen, nitro or cyano groups.

In this description, substituted hydrocarbyls are defined as chains or links that may comprise one or more heteroatoms.

Preferably, $R_1$, $R_5$, $R_6$, $R_7$, $R_{10}$ and $R_{12}$ are each independently selected from hydrogen or substituted or unsubstituted alkyl or aryl groups or halogen.

The preferred alkyl groups are methyl and tert-butyl.

The preferred aryl groups are unsubstituted or substituted phenyl groups.

The preferred halogen is chlorine.

Preferably all three $R_1$, $R_6$ and $R_7$ are not hydrogen simultaneously.

More preferably either $R_6$ or $R_7$ is present, the other being hydrogen, and $R_1$ is hydrogen or one of the preferred substituent groups described hereabove.

Preferably M is Ti, Zr, Hf, V, Cr, Mn, Fe, Co, Ni, Pd or rare earths. More preferably, it is Ti, Cr, Fe or Zr.

Preferably X is halogen, more preferably it is chlorine.

The solvent may be selected from dichloromethane or tetrahydrofuran and the complexation reaction is carried out at room temperature or at reflux.

The present invention further discloses an active catalyst system comprising the single site catalyst component of formula I or I' and an activating agent having an ionising action.

Suitable activating agents are well known in the art. The activating agent can be an aluminium alkyl represented by formula $AlR^+_n X_{3-n}$ wherein $R^+$ is an alkyl having from 1 to 20 carbon atoms and X is a halogen. The preferred alkylating agents are triisobutyl aluminium (TIBAL) or triethyl aluminium (TEAL).

Alternatively, it can be aluminoxane and comprise oligomeric linear and/or cyclic alkyl aluminoxanes represented by formula

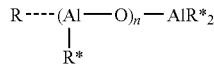

for oligomeric, linear aluminoxanes and by formula

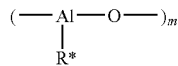

for oligomeric, cyclic aluminoxane,
wherein n is 1-40, preferably 10-20, m is 3-40, preferably 3-20 and R* is a $C_1$-$C_8$ alkyl group and preferably methyl.

The amount of activating agent is selected to give an Al/M ratio of from 100 to 3000, preferably of from 500 to 2000. The amount of activating agent depends upon its nature: for IBAO the preferred Al/M ratio is of about 500, and for MAO, it is about 2000.

Suitable boron-containing activating agents may comprise a triphenylcarbenium boronate such as tetrakis-pentafluorophenyl-borato-triphenylcarbenium as described in EP-A-0427696, or those of the general formula [L'-H]+[B $Ar_1$ $Ar_2$ $X_3$ $X_4$]— as described in EP-A-0277004 (page 6, line 30 to page 7, line 7). The amount of boron-containing activating agent is selected to give B/M ratio of from 0.5 to 5, preferably of about 1.

In another embodiment, according to the present invention, the single site catalyst component of formula I may be deposited on a conventional support. Preferably, the conventional support is silica impregnated with MAO. Alternatively and preferably, it can be an activating support such as fluorinated alumina silica.

The present invention further discloses a method for preparing an active catalyst system that comprises the steps of:
a) providing a ligand of formula II or II';
b) complexing the ligand of step a) with a metallic salt $MX_{n+2}$ in a solvent;
c) retrieving catalyst component I or I';
d) activating the catalyst component of step c) with an activating agent having an ionising action;
e) optionally adding a cocatalyst;
f) retrieving an active oligomerisation or polymerisation catalyst system.

Alternatively, in step d) catalyst component I or I' is deposited on a support impregnated with an activating agent or on a fluor containing activating support.

The cocatalyst may be selected from triethylaluminium, triisobutylaluminum, tris-n-octylaluminium, tetraisobutyldialuminoxane or diethyl zinc.

The active catalyst system is used in the oligomerisation and in the polymerisation of ethylene and alpha-olefins.

The present invention discloses a method for the oligomerisation or the homo- or co-polymerisation of ethylene and alpha-olefins that comprises the steps of:
a) injecting the active catalyst system into the reactor; and
b) injecting the monomer and optional comonomer either before or after or simultaneously with step a);
c) maintaining under polymerisation conditions;
d) retrieving the oligomers and/or polymer.

The pressure in the reactor can vary from 0.5 to 50 bars, preferably from 5 to 25 bars.

The polymerisation temperature can range from 10 to 100° C., preferably from 50 to 85° C.

Preferably the monomer and optional comonomer are selected from ethylene, propylene or 1-hexene.

In another preferred embodiment according to the present invention, the optional comonomer is a polar functionalised alpha-olefin.

EXAMPLES

All reactions were performed using standard Schlenk techniques or in an argon-filled glove-box. The starting materials and reagents, purchased from commercial suppliers, were used without purification. All the solvents were dried and distilled before use either over sodium and benzophenone for toluene, pentane and THF, or over $CaH_2$ for ethanol. $^1H$, $^{13}C$ NMR spectra were recorded on a Bruker Advance300 apparatus.
Preparation of Ligands.
I. Ligands.
General Procedure.

2 mmol of 2-pyrrolcarboxaldehyde (reagent 1) and 2 mmol of 2-aminophenol (reagent 2) were dissolved in 10 mL of dry ethanol. One drop of glacial acetic acid was added and the reaction mixture was stirred during 12 h. The solution was filtered and the solid was washed with 3 ml of dry ethanol. Ligands were obtained as a solid.

Synthesis of ligand 2-(pyrrolyl-methyleneimino)-phenol (L1)

Ligand L1 was prepared following the general procedure and 2-amino-phenol was used as reagent 2. Ligand L1 was obtained with a yield of 92%.

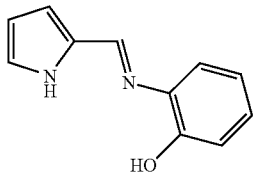 [SMILES: Oc1ccccc1/N=C/c1ccc[nH]1]

$^1$H NMR (300 MHz, DMSO d6) δ (ppm): 6.21 (s, 1H), 6.69 (s, 1H), 6.79-6.87 (m, 2H), 7.02 (m, 1H), 7.13 (s, 1H), 7.33 (d, J=9 Hz, 1H), 8.55 (s, 1H), 8.78 (bs, 1H), 11.80 (s, 1H).

Synthesis of ligand 2-(pyrrolyl-methyleneimino)-4-methyl-phenol (L2)

Ligand L2 was prepared following the same procedure as that used to prepare ligand L1 except that 2-amino-4-methyl-phenol was used as reagent 2. Ligand L2 was obtained with a yield of 94%.

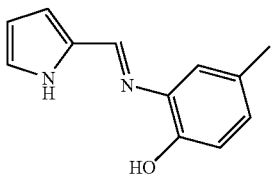

$^1$H NMR (300 MHz, DMSO d6) δ (ppm): 2.21 (s, 3H), 5.75 (s, 1H), 6.65 (d, J=3 Hz, 1H), 6.73 (d, J=9 Hz, 1H), 6.82 (d, J=3 Hz, 1H), 7.16 (d, J=9 Hz, 2H), 8.54 (bs, 2H), 11.78 (s, 1H).

Synthesis of ligand 2-(pyrrolyl-methyleneimino)-5-methyl-phenol (L3)

Ligand L3 was prepared following the same procedure as that used to prepare ligand L1 except that 2-amino-5-methyl-phenol was used as reagent 2. Ligand L3 was obtained with a yield of 93%.

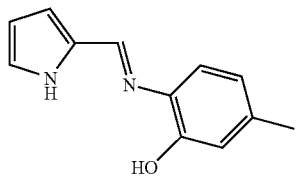

$^1$H NMR (300 MHz, DMSO d6) δ (ppm): 2.22 (s, 3H), 6.20 (s, 1H), 6.50-6.80 (m, 3H), 7.11 (s, 1H), 7.23 (d, J=9 Hz, 1H), 8.52 (s, 1H), 8.66 (s, 1H), 11.74 (s, 1H).

Synthesis of ligand 2-(pyrrolyl-methyleneimino)-4-tertbutyl-phenol (L4)

Ligand L4 was prepared following the same procedure as that used to prepare ligand L1 except that 2-amino-4-tertbutyl-phenol was used as reagent 2. Ligand L4 was obtained with a yield of 90%.

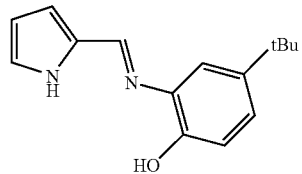 [SMILES: CC(C)(C)c1ccc(O)c(/N=C/c2ccc[nH]2)c1]

$^1$H NMR (300 MHz, DMSO d6) δ (ppm): 1.26 (s, 9H), 6.20 (s, 1H), 6.66 (s, 1H), 6.78 (d, J=9 Hz, 1H), 7.05 (d, J=9 Hz, 1H), 7.11 (s, 1H), 7.32 (s, 1H), 8.61 (s, 2H), 11.77 (s, 1H).

Synthesis of ligand 2-(pyrrolyl-methyleneimino)-4-chloro-phenol (L5)

Ligand L5 was prepared following the same procedure as that used to prepare ligand L1 except that 2-amino-4-chloro-phenol was used as reagent 2. Ligand L5 was obtained with a yield of 97%.

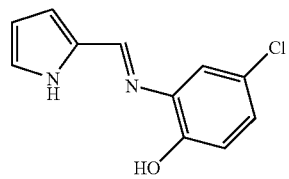 [SMILES: Oc1ccc(Cl)cc1/N=C/c1ccc[nH]1]

$^1$H NMR (300 MHz, DMSO d6) δ (ppm): 6.22 (s, 1H), 6.69 (s, 1H), 6.85 (d, J=9 Hz, 1H), 7.05 (d, J=9 Hz, 1H), 7.16 (s, 1H), 7.40 (s, 1H), 8.58 (s, 1H), 8.97 (s, 1H), 11.82 (s, 1H).

Synthesis of ligand 2-(pyrrolyl-methyleneimino)-4-phenyl-phenol (L6)

Ligand L6 was prepared following the same procedure as that used to prepare ligand L1 except that 2-amino-4-phenyl-phenol was used as reagent 2. Ligand L6 was obtained with a yield of 93%.

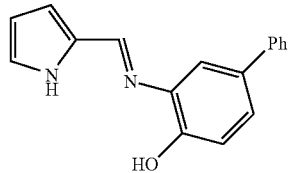 [SMILES: Oc1ccc(-c2ccccc2)cc1/N=C/c1ccc[nH]1]

$^1$H NMR (300 MHz, DMSO d6) δ (ppm): 6.22 (s, 1H), 6.69 (s, 1H), 6.94 (d, J=9 Hz, 1H), 7.15 (s, 1H), 7.28-7.65 (m, 7H), 8.73 (s, 1H), 8.90 (s, 1H), 11.82 (s, 1H).

Synthesis of ligand 2-(pyrrolyl-methyleneimino)-3-methyl-phenol (L7)

Ligand L7 was prepared following the same procedure as that used to prepare ligand L1 except that 2-amino-3-methyl-phenol was used as reagent 2. Ligand L7 was obtained with a yield of 99%.

¹H NMR (300 MHz, DMSO d6) δ (ppm): 2.15 (s, 3H), 6.18 (s, 1H), 6.77-6.59 (m, 4H), 7.01 (s, 1H), 8.22 (s, 1H), 9.0 (bs, 1H), 11.65 (s, 1H).

Synthesis of ligand
2-(pyrrolyl-methyleneimino)-4-nitro-phenol (L8)

Ligand L8 was prepared following the same procedure as that used to prepare ligand L1 except that 2-amino-4-nitro-phenol was used as reagent 2. Ligand L8 was obtained with a yield of 92%.

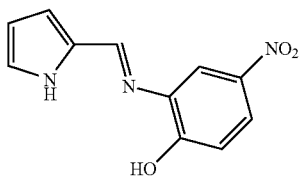 [SMILES: O=[N+]([O-])c1ccc(O)c(/N=C/c2ccc[nH]2)c1]

¹H NMR (300 MHz, DMSO d6) δ (ppm): 6.25 (s, 1H), 6.78 (d, J=3 Hz, 1H), 7.03 (d, J=9 Hz, 1H), 7.20 (s, 1H), 7.96 (d, J=9 Hz, 1H), 8.18 (d, J=3 Hz, 1H), 8.69 (s, 1H), 10.12 (bs, 1H), 11.84 (s, 1H).
$^{13}$C{¹H} NMR (75 MHz, DMSO d6) δ (ppm): 110.7, 113.2, 115.8, 118.0, 122.9, 125.2, 131.3, 137.5, 140.5, 150.6, 158.7.

II. Preparation of Metallic Complexes.

Synthesis of Titanium Ti(IV) Complexes 1 mmol of ligand was dissolved in 5 mL of THF and cooled to a temperature of −78° C. 2 mmol of n-butyl lithium (1.6 M in hexane) was added drop-wise. The solution was stirred for 2 hours at room temperature. 1 mmol of TiCl$_4$ (1M in toluene) was dissolved in 5 mL of THF and cooled to a temperature of −78° C. The solution of the anionic ligand was added drop-wise to the solution of TiCl$_4$. The resulting solution was stirred overnight at room temperature. The mixture was evaporated to dryness and the complex was extracted with 10 mL of dry dichloromethane. The filtrate was evaporated and the residue was washed with 3 mL of diethyl ether, with 10 mL of pentane, and with another 10 mL of pentane. The resulting solid was dried under vacuum to afford metallic complex as powder.

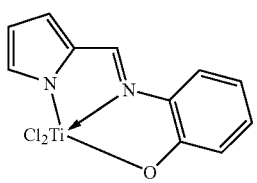

Ligand L1 was used to prepare complex A1 with a yield of 82%.

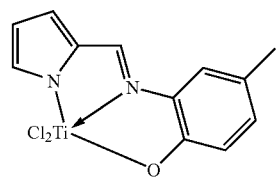

Ligand L2 was used to prepare complex A2 with a yield of 91%.

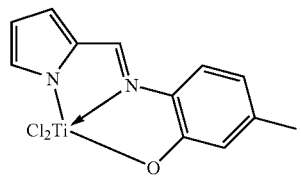

Ligand L3 was used to prepare complex A3 with a yield of 90%.

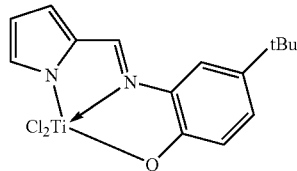

Ligand L4 was used to prepare complex A4 with a yield of 90%.

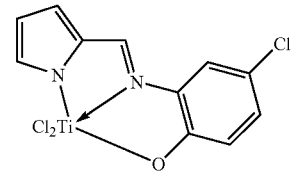

Ligand L5 was used to prepare complex A5 with a yield of 93%.

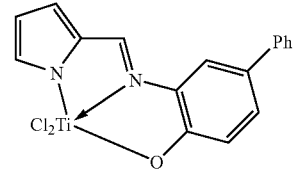

Ligand L6 was used to prepare complex A6 with a yield of 90%.

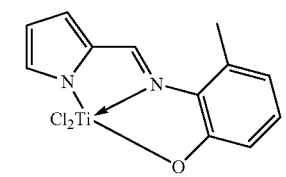

Ligand L7 was used to prepare complex A7 with a yield of 47%.

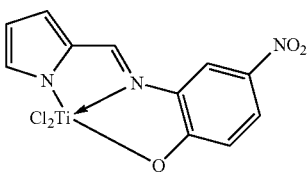

Ligand L8 was used to prepare complex A8 with a yield of 42%.

Synthesis of Chromium Cr(III) Complexes 1 mmol of ligand was dissolved in 5 mL of THF and cooled to a temperature of −15° C. 2 mmol of n-butyl lithium (1.6 M in hexane) was added drop-wise. The solution was stirred for 30 minutes and added to a solution of 1 mmol of $(THF)_3CrCl_3$ dissolved in 5 mL of THF. The resulting solution was stirred overnight at room temperature. The mixture was concentrated to approximately 2 mL and 10 mL of pentane were added. Solvents were filtered off and the solid was washed twice with pentane. The resulting solid was dried under vacuum to afford metallic complex as a powder.

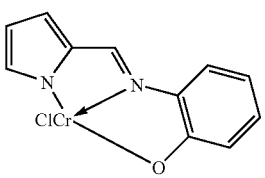

Ligand L1 was used to prepare complex B1 with a yield of 99%.

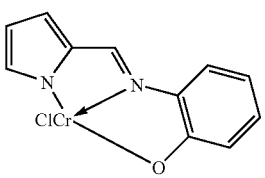

Ligand L2 was used to prepare complex B2 with a yield of 91%.

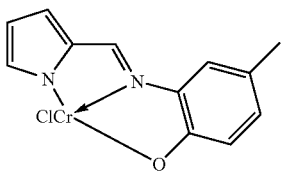

Ligand L3 was used to prepare complex B3 with a yield of 92%.

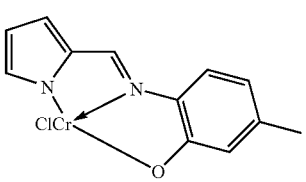

Ligand L4 was used to prepare complex B4 with a yield of 99%.

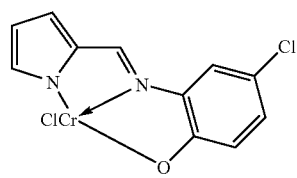

Ligand L5 was used to prepare complex B5 with a yield of 99%.

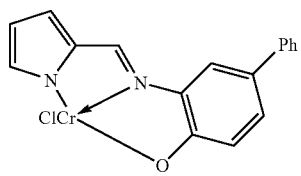

Ligand L6 was used to prepare complex B6 with a yield of 93%.

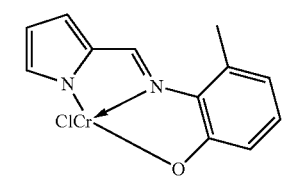

Ligand L7 was used to prepare complex B7 with a yield of 93%.

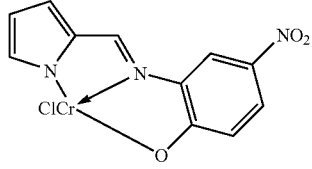

Ligand L8 was used to prepare complex B8 with a yield of 97%.

Synthesis of Zirconium Zr(IV) Complex 1 mmol of ligand L1 was dissolved in 5 mL of THF and cooled to a temperature of −78° C. 2 mmol of n-butyl lithium (1.6 M in hexane) was added drop-wise. The solution was stirred for 2 hours at room temperature. 1 mmol of $ZrCl_4$ was dissolved in 5 mL of THF and cooled to a temperature of −78° C. The solution of the anionic ligand was added drop-wise to the solution of $ZrCl_4$. The resulting solution was stirred overnight at room temperature. The mixture was evaporated to dryness and the complex was extracted with 10 mL of dry dichloromethane. The filtrate was evaporated and the residue was washed with 3 mL of diethyl ether, with 10 mL of pentane, and with another 10 mL of pentane. The resulting solid was dried under vacuum to afford complex C1 as powder with 71% yield.

Synthesis of Vanadium V(III) Complex 1 mmol of ligand L1 was dissolved in 5 mL of THF and cooled to a temperature of −78° C. 2 mmol of n-butyl lithium (1.6 M in hexane) was added drop-wise. The solution was stirred for 2 hours at room temperature: 1 mmol of $(THF)_3 VCl_3$ was dissolved in 5 mL of THF and cooled to a temperature of −78° C. The solution of the anionic ligand was added drop-wise to the solution of $VCl_3$. The resulting solution was stirred overnight at room temperature. The mixture was evaporated to dryness and the complex was extracted with 10 mL of dry dichloromethane. The filtrate was evaporated and the residue was washed with 3 mL of diethyl ether, with 10 mL of pentane, and with another 10 mL of pentane. The resulting solid was dried under vacuum to afford complex D1 as powder with 72% yield.

III. Polymerisation of Ethylene.

Polymerisation reactions were realised on a 24 parallel reactor unit containing glass inserts of 50 ml with magnetic stirrers. In a glove box, 0.5 mg of metallic complex were introduced into a vial. Then 0.6 ml of methylaluminoxane (MAO) (30 wt % in toluene) and 24 ml of heptane were added. The vials were crimped with a septum and installed into the reactor unit heated at a temperature of 60° C. The vials' septa were pierced by the needles of the reactor unit. Stirring was started and regulated at a speed of 1000 rpm. Then ethylene was injected and the pressure was regulated at 22 bar while the temperature was increased to 80° C. These conditions were maintained during 30 min., then the reactors were depressurised and cooled down. The vials were opened and an acidic alcoholic solution was added. The polymers were filtered, washed and dried. The results are displayed in Table I.

TABLE I

| Catalyst | Mass cata g | Amount cata μmol | Mass PE g | Activity Kg/mmol/h | Tm ° C. |
|---|---|---|---|---|---|
| A8 | 0.58 | 1.65 | 0.78 | 0.94 | 134.9 |
| A7 | 0.50 | 1.57 | 1.38 | 1.75 | 134.2 |
| A6 | 0.51 | 1.34 | 1.31 | 1.95 | 133.8 |
| A5 | 0.50 | 1.48 | 1.53 | 2.07 | 133.6 |
| A1 | 0.55 | 1.81 | 1.28 | 1.42 | 134.1 |
| A2 | 0.50 | 1.56 | 1.45 | 1.85 | 133.9 |
| A3 | 0.58 | 1.82 | 0.79 | 0.87 | 134 |
| A4 | 0.49 | 1.35 | 1.42 | 2.10 | 134.3 |
| C1 | 1.27 | 3.67 | 0.65 [a; b] | 0.54 | 131.8 |
| D1 | 0.93 | 3.43 | 0.67 [a; c] | 0.59 | 128.6 |
| A1 | 0.49 | 1.62 | 0.95 [a] | 1.78 | 133.3 |

[a] 20 min. instead of 30 min.
[b] 1.2 ml of MAO instead of 0.6 ml
[c] 1.5 ml of MAO instead of 0.6 ml

IV. Polymerisation of Ethylene with a Supported Catalyst System.

Complex A8 was deposited on a MAO impregnated silica (Sylopol 952X1836), with 2.2 wt % of complex based on the total weight of the obtained supported catalyst. This supported catalyst was used for the polymerisation of ethylene.

Ethylene polymerisation reactions were carried out in a 130 ml stainless steel autoclave equipped with mechanical stirring and a stainless steel injection cylinder. In a typical reaction run, the reactor was first dried under nitrogen flow at 100° C. during 10 min. Then it was cooled down to the reaction temperature of 85° C., and 35 ml of isobutane were introduced into the reactor with a syringe pump, followed by the comonomer if required. The pressure was adjusted to the desired value of 29 bars, with ethylene. In an argon-filled glove box, 100 mg of the supported catalyst, 0.29 ml of TiBAl (10% in n-hexane) and 0.5 ml of n-heptane were placed into the injection cylinder. The valve was closed and the cylinder was connected to the reactor under nitrogen flow. The active catalyst mixture was then introduced into the reactor with 40 ml of isobutane. After 1 hour at 750 rpm, the reactor was cooled down to room temperature and slowly depressurised. The polymer was recovered and characterised by DSC. The polymerisation results are displayed in Table II.

TABLE II

| Supported complex | Hexene ml | $H_2$ NI | PE g | Activity* g/g/h | Tm (° C.) |
|---|---|---|---|---|---|
| A8 | / | / | 1.3 | 13 | 132 |
| A8 | / | 0.02 | 1.4 | 13.8 | 132 |
| A8 | 2.4 | 0.02 | 1.2 | 12 | 117 |

*Activity is expressed as g of polyethylene per g of supported catalyst per hour.

Due to the high molecular weight of the obtained polymers, GPC analysis were not possible, even in TCB at 135° C.

The invention claimed is:

1. An active catalyst system consisting essentially of:
a metallic complex represented by general formula I wherein $R_1$, $R_2$, $R_3$, $R_4$, $R_5$, $R_6$, $R_7$, $R_8$, $R_9$, $R_{10}$, $R_{11}$ and $R_{12}$ are each independently selected from hydrogen, $C_1$ to $C_{20}$ hydrocarbyls or inert functional groups and wherein two or more of those groups can be linked together to form rings, M is a metal of Group 3 to 10 of the Periodic Table, Y is O, each X is independently selected from halogens, m is zero or an integer from 1 to 3, (n+2) is the valence of M; and
wherein

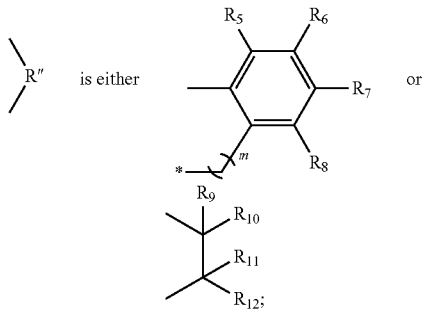 is either and
an activating agent that is an aluminum-containing complex, wherein the active catalyst system comprises an Al/M ratio ranging from 100 to 3000, wherein at least one of $R_1$, $R_6$ and $R_7$ is not hydrogen.

2. The active catalyst system of claim 1, wherein m is zero and $R_2$, $R_3$, $R_4$, $R_8$, $R_9$ and $R_{11}$ are the same and are hydrogen.

3. The active catalyst system of claim 1, wherein $R_1$, $R_5$, $R_6$, $R_7$, $R_{10}$ and $R_{12}$ are each independently selected from hydrogen, alkyl groups, aryl groups, halogen, nitro or cyano groups.

4. A method for preparing the active catalyst system of claim 1 comprising:
   providing the metallic complex represented by general formula I;
   activating the metallic complex with the activating agent having ionising action;
   optionally adding a cocatalyst; and
   retrieving an active oligomerisation or polymerisation catalyst system.

5. A method for oligomerising or homo- or co-polymerising ethylene and alpha-olefins comprising:
   injecting the active catalyst system of claim 1 into a reactor;
   injecting a monomer and optional comonomer into the reactor;
   maintaining under polymerisation conditions; and
   retrieving oligomers or polymer.

6. The method of claim 5, wherein the monomer or optional comonomer are selected from ethylene, propylene or 1-hexene.

7. An active catalyst system consisting essentially of:
   a metallic complex represented by general formula I

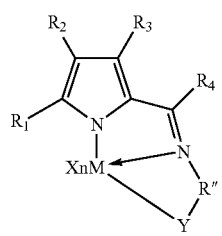

(I)

wherein $R_1$, $R_2$, $R_3$, $R_4$, $R_5$, $R_6$, $R_7$, $R_8$, $R_9$, $R_{10}$, $R_{11}$ and $R_{12}$ are each independently selected from hydrogen, $C_1$ to $C_{20}$ hydrocarbyls or inert functional groups and wherein two or more of those groups can be linked together to form rings, M is a metal of Group 3 to 10 of the Periodic Table, Y is O, each X is Cl, m is zero or an integer from 1 to 3, (n+2) is the valence of M; and
wherein

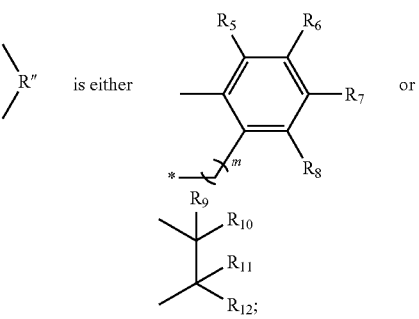 is either and
an activating agent that is an aluminum-containing complex, wherein the active catalyst system comprises an Al/M ratio ranging from 100 to 3000.

8. A method for preparing the active catalyst system of claim 7 comprising:
   providing the metallic complex represented by general formula I;
   activating the metallic complex with the activating agent having ionising action;
   optionally adding a cocatalyst; and
   retrieving an active oligomerisation or polymerisation catalyst system.

9. A method for oligomerising or homo- or co-polymerising ethylene and alpha-olefins comprising:
   injecting the active catalyst system of claim 7 into a reactor;
   injecting a monomer and optional comonomer into the reactor;
   maintaining under polymerisation conditions; and
   retrieving oligomers or polymer.

10. An active catalyst system consisting essentially of:
   a metallic complex represented by general formula I

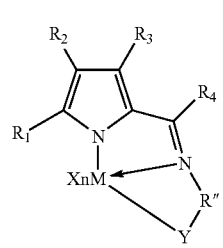

(I)

wherein $R_1$, $R_2$, $R_3$, $R_4$, $R_5$, $R_6$, $R_7$, $R_8$, $R_9$, $R_{10}$, $R_{11}$ and $R_{12}$ are each independently selected from hydrogen, $C_1$ to $C_{20}$ hydrocarbyls or inert functional groups and wherein two or more of those groups can be linked together to form rings, M is a metal of Group 3 to 10 of the Periodic Table, Y is O, each X is independently selected from halogens, m is zero or an integer from 1 to 3, (n+2) is the valence of M; and wherein

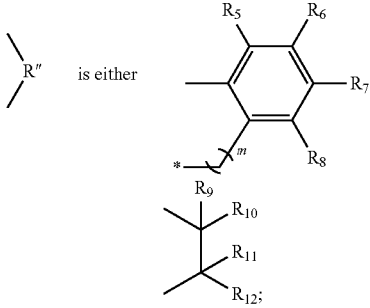

and an activating agent that is an aluminum-containing complex, wherein the active catalyst system comprises an Al/M ratio ranging from 100 to 3000, wherein at least one of $R_1$, $R_{10}$ and $R_{12}$ is not hydrogen.

11. A method for preparing the active catalyst system of claim 10 comprising:

providing the metallic complex represented by general formula I;

activating the metallic complex with the activating agent having ionising action;

optionally adding a cocatalyst; and retrieving an active oligomerisation or polymerisation catalyst system.

12. A method for oligomerising or homo- or co-polymerising ethylene and alpha-olefins comprising:

injecting the active catalyst system of claim 10 into a reactor;

injecting a monomer and optional comonomer into the reactor;

maintaining under polymerisation conditions; and retrieving oligomers or polymer.

13. An active catalyst system consisting essentially of:

a metallic complex represented by general formula I

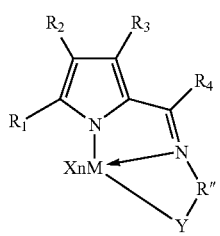

(I)

wherein $R_1$, $R_2$, $R_3$, $R_4$, $R_5$, $R_6$, $R_7$, $R_8$, $R_9$, $R_{10}$, $R_{11}$ and $R_{12}$ are each independently selected from hydrogen, $C_1$ to $C_{20}$ hydrocarbyls or inert functional groups and wherein two or more of those groups can be linked together to form rings, M is a metal of Group 3 to 10 of the Periodic Table, Y is O, each X is independently selected from halogens, m is zero or an integer from 1 to 3, (n+2) is the valence of M; and wherein

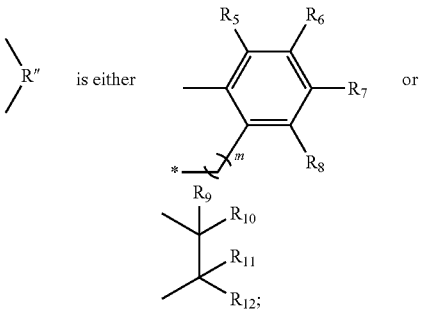

and an activating agent that is an aluminum-containing complex, wherein the active catalyst system comprises an Al/M ratio ranging from 100 to 3000, wherein the aluminum-containing complex is triisobutyl aluminum, triethyl aluminum, or aluminoxane.

14. The active catalyst system of claim 13, wherein the aluminum-containing complex is triisobutyl aluminum or aluminoxane.

15. A method for preparing the active catalyst system of claim 13 comprising:

providing the metallic complex represented by general formula I;

activating the metallic complex with the activating agent having ionising action;

optionally adding a cocatalyst; and retrieving an active oligomerisation or polymerisation catalyst system.

16. A method for oligomerising or homo- or co-polymerising ethylene and alpha-olefins comprising:

injecting the active catalyst system of claim 13 into a reactor;

injecting a monomer and optional comonomer into the reactor;

maintaining under polymerisation conditions; and retrieving oligomers or polymer.

17. An active catalyst system consisting essentially of:

a metallic complex represented by general formula I

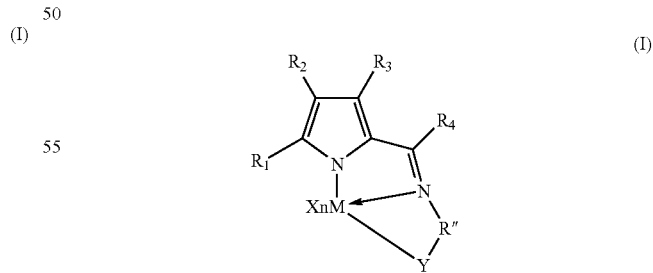

(I)

wherein $R_1$, $R_2$, $R_3$, $R_4$, $R_5$, $R_6$, $R_7$, $R_8$, $R_9$, $R_{10}$, $R_{11}$ and $R_{12}$ are each independently selected from hydrogen, $C_1$ to $C_{20}$ hydrocarbyls or inert functional groups and wherein two or more of those groups can be linked together to form rings, wherein M is Ti, Cr, Zr or Fe, wherein Y is O, each X is independently selected from halogens, m is zero or an integer from 1 to 3, (n+2) is the valence of M; and wherein R″ is either

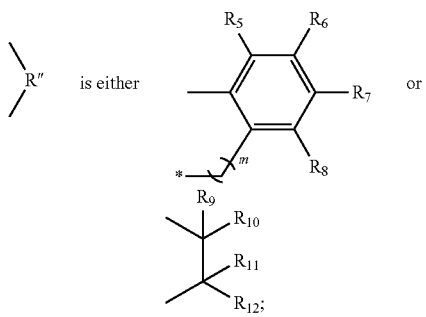

and an activating agent that is an aluminum-containing complex, wherein the active catalyst system comprises an Al/M ratio ranging from 100 to 3000.

18. The active catalyst system of claim 17, wherein M is Zr.

19. A method for preparing the active catalyst system of claim 17 comprising:
providing the metallic complex represented by general formula I;
activating the metallic complex with the activating agent having ionising action;
optionally adding a cocatalyst; and
retrieving an active oligomerisation or polymerisation catalyst system.

20. A method for oligomerising or homo- or co-polymerising ethylene and alpha-olefins comprising:
injecting the active catalyst system of claim 17 into a reactor;
injecting a monomer and optional comonomer into the reactor;
maintaining under polymerisation conditions; and
retrieving oligomers or polymer.

21. An active catalyst system consisting essentially of:
a metallic complex represented by general formula I

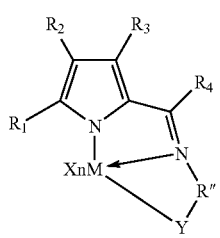

(I)

wherein $R_1$, $R_2$, $R_3$, $R_4$, $R_5$, $R_6$, $R_7$, $R_8$, $R_9$, $R_{10}$, $R_{11}$ and $R_{12}$ are each independently selected from hydrogen, $C_1$ to $C_{20}$ hydrocarbyls or inert functional groups and wherein two or more of those groups can be linked together to form rings, M is Ti, Cr, Zr or Fe, Y is O or NR*, with R* being alkyl or aryl group having from 1 to 12 carbon atoms, each X is independently selected from halogens, m is zero or an integer from 1 to 3, (n+2) is the valence of M; and wherein R″ is either

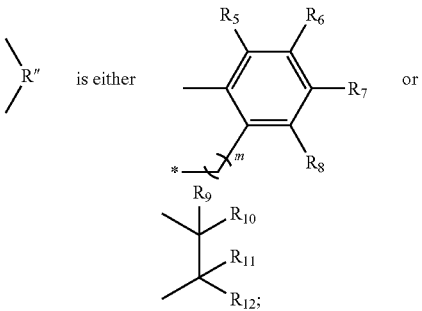

an activating agent that is an aluminum-containing complex, wherein the active catalyst system comprises an Al/M ratio ranging from 100 to 3000; and
a co-catalyst.

22. The active catalyst system of claim 21, wherein m is zero and $R_2$, $R_3$, $R_4$, $R_8$, $R_9$ and $R_{11}$ are the same and are hydrogen.

23. The active catalyst system of claim 21, wherein $R_1$, $R_5$, $R_6$, $R_7$, $R_{10}$ and $R_{12}$ are each independently selected from hydrogen, alkyl groups, aryl groups, halogen, nitro or cyano groups.

24. The active catalyst system of claim 21, wherein at least one of $R_1$, $R_6$, and $R_7$ is not hydrogen.

25. The active catalyst system of claim 21, wherein X is Cl.

26. The active catalyst system of claim 21, wherein at least one of $R_1$, $R_{10}$ and $R_{12}$ is not hydrogen.

27. A method for preparing the active catalyst system of claim 21 comprising:
providing the metallic complex represented by general formula I;
activating the metallic complex with the activating agent having ionising action;
optionally adding a cocatalyst; and
retrieving an active oligomerisation or polymerisation catalyst system.

28. A method for oligomerising or homo- or co-polymerising ethylene and alpha-olefins comprising:
injecting the active catalyst system of claim 21 into a reactor;
injecting a monomer and optional comonomer into the reactor;
maintaining under polymerisation conditions; and
retrieving oligomers or polymer.

29. An active catalyst system consisting essentially of:
a metallic complex represented by general formula I

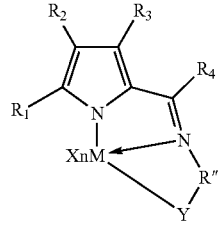

(I)

wherein $R_1$, $R_2$, $R_3$, $R_4$, $R_5$, $R_6$, $R_7$, $R_8$, $R_9$, $R_{10}$, $R_{11}$ and $R_{12}$ are each independently selected from hydrogen, $C_1$ to $C_{20}$ hydrocarbyls or inert functional groups and wherein two or more of those groups can be linked together to form rings, M is a metal of Group 3 to 10 of the Periodic Table, Y is O, each X is independently selected from halogens, m is zero or an integer from 1 to 3, (n+2) is the valence of M; and
wherein

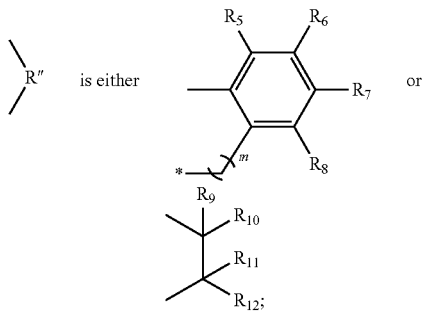

and
an activating agent that is a boron containing complex, wherein the boron containing complex is selected from a triphenylcarbenium boronate or a boron containing complex of the formula:

wherein L' is a neutral Lewis base; H is a hydrogen atom; [L'-H]+ is a Bronsted acid; B is boron in a valence state of 3; $Ar_1$ and $Ar_2$ are the same or different aromatic or substituted-aromatic hydrocarbon radicals containing from 6 to 20 carbon atoms; and wherein $X_3$ and $X_4$ are radicals independently selected from the group consisting of hydride radicals, halide radicals with the proviso that only one of $X_3$ or $X_4$ can be a halide radical, hydrocarbyl radicals containing from 1 to 20 carbon atoms, substituted-hydrocarbyl radicals, and hydrocarbyl-substituted metal radicals.

30. The active catalyst system of claim 29, wherein the boron containing complex is tetrakis-pentafluorophenyl-borato-triphenylcarbenium.

31. A method for preparing the active catalyst system of claim 29 comprising:
providing the metallic complex represented by general formula I;
activating the metallic complex with the activating agent having ionising action;
optionally adding a cocatalyst; and
retrieving an active oligomerisation or polymerisation catalyst system.

32. A method for oligomerising or homo- or co-polymerising ethylene and alpha-olefins comprising:
injecting the active catalyst system of claim 29 into a reactor;
injecting a monomer and optional comonomer into the reactor;
maintaining under polymerisation conditions; and
retrieving oligomers or polymer.

33. An active catalyst system consisting essentially of:
a metallic complex represented by general formula I

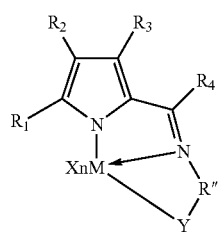

(I)

wherein $R_1$, $R_2$, $R_3$, $R_4$, $R_5$, $R_6$, $R_7$, $R_8$, $R_9$, $R_{10}$, $R_{11}$ and $R_{12}$ are each independently selected from hydrogen, $C_1$ to $C_{20}$ hydrocarbyls or inert functional groups and wherein two or more of those groups can be linked together to form rings, M is Ti, Cr, Zr or Fe, Y is O or NR*, with R* being alkyl or aryl group having from 1 to 12 carbon atoms, each X is independently selected from halogens, m is zero or an integer from 1 to 3, (n+2) is the valence of M; and
wherein

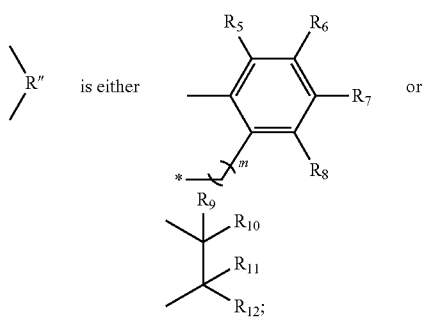

an activating agent that is a boron containing complex, wherein the boron containing complex is selected from a triphenylcarbenium boronate or a boron containing complex of the formula:

wherein L' is a neutral Lewis base; H is a hydrogen atom; [L'-H]+ is a Bronsted acid; B is boron in a valence state of 3; $Ar_1$ and $Ar_2$ are the same or different aromatic or substituted-aromatic hydrocarbon radicals containing from 6 to 20 carbon atoms; and wherein $X_3$ and $X_4$ are radicals independently selected from the group consisting of hydride radicals, halide radicals with the proviso that only one of $X_3$ or $X_4$ can be a halide radical, hydrocarbyl radicals containing from 1 to 20 carbon atoms, substituted-hydrocarbyl radicals, and hydrocarbyl-substituted metal radicals; and
a co-catalyst.

34. The active catalyst system of claim 33, wherein the boron containing complex is tetrakis-pentafluorophenyl-borato-triphenylcarbenium.

35. A method for preparing the active catalyst system of claim 33 comprising:
providing the metallic complex represented by general formula I;
activating the metallic complex with the activating agent having ionising action;
optionally adding a cocatalyst; and
retrieving an active oligomerisation or polymerisation catalyst system.

36. A method for oligomerising or homo- or co-polymerising ethylene and alpha-olefins comprising:
injecting the active catalyst system of claim 33 into a reactor;
injecting a monomer and optional comonomer into the reactor;
maintaining under polymerisation conditions; and
retrieving oligomers or polymer.

* * * * *